US012588948B2

(12) United States Patent
May et al.

(10) Patent No.: US 12,588,948 B2
(45) Date of Patent: Mar. 31, 2026

(54) FLUID-COOLED LOW-PROFILE MICROWAVE ABLATION PROBE WITH SPHERICAL ABLATION ZONE

(71) Applicant: Varian Medical Systems, Inc., Palo Alto, CA (US)

(72) Inventors: Justin Patrick May, Austin, TX (US); Hojjatollah Fallahi, Saint Paul, MN (US)

(73) Assignee: Walmart Apollo, LLC, Bentonville, AR (US)

( * ) Notice: Subject to any disclaimer, the term of this patent is extended or adjusted under 35 U.S.C. 154(b) by 928 days.

(21) Appl. No.: 17/808,862

(22) Filed: Jun. 24, 2022

(65) Prior Publication Data

US 2023/0414281 A1    Dec. 28, 2023

(51) Int. Cl.
A61B 18/18          (2006.01)
A61B 18/00          (2006.01)

(52) U.S. Cl.
CPC ..................... A61B 18/1815 (2013.01); *A61B 2018/00005* (2013.01); *A61B 2018/00095* (2013.01); *A61B 2018/00101* (2013.01)

(58) Field of Classification Search
CPC ...... A61B 18/1815; A61B 2018/00005; A61B 2018/00095; A61B 2018/00101; A61B 2018/00023; A61B 2018/1838; A61B 2018/1853; A61B 2018/1869; A61B 2018/00011; A61B 2018/00059; A61B 2018/00577; A61B 2018/183
See application file for complete search history.

(56) References Cited

U.S. PATENT DOCUMENTS

| | | | |
|---|---|---|---|
| 2010/0305559 A1* | 12/2010 | Brannan ............ | A61B 18/1815 606/33 |
| 2013/0245412 A1* | 9/2013 | Rong ................. | A61B 5/14532 600/347 |
| 2014/0296839 A1* | 10/2014 | Brannan ............ | A61B 18/1815 606/33 |
| 2018/0036069 A1* | 2/2018 | Dickhans ........... | A61B 18/1492 |
| 2018/0214205 A1* | 8/2018 | Williams ........... | A61B 18/1815 |
| 2018/0235697 A1 | 8/2018 | Brannan et al. | |
| 2020/0188021 A1* | 6/2020 | Wong ..................... | A61B 34/30 |
| 2020/0222105 A1* | 7/2020 | Cao ......................... | A61B 18/14 |
| 2020/0289200 A1 | 9/2020 | Brannan et al. | |
| 2021/0161586 A1* | 6/2021 | Eaton-Evans ........ | A61B 1/2676 |

* cited by examiner

*Primary Examiner* — Ankit D Tejani
*Assistant Examiner* — Joshua Brendon Solomon
(74) *Attorney, Agent, or Firm* — Morgan, Lewis & Bockius LLP; Manita Rawat

(57)          ABSTRACT

A microwave ablation probe includes a cable extending in an axial direction and also includes an antenna configured to deliver Radio Frequency (RF) energy. The probe includes a shell positioned radially outward of the cable and a choke electrically coupled to an outer conductor of the cable. The probe also includes a cooling tube positioned inside the shell and positioned radially outward of the cable. The cooling tube including a first portion with a first outer diameter and a second portion with a second outer diameter. The second portion located radially outward of the choke and the second outer diameter being greater than the first outer diameter.

20 Claims, 11 Drawing Sheets

100

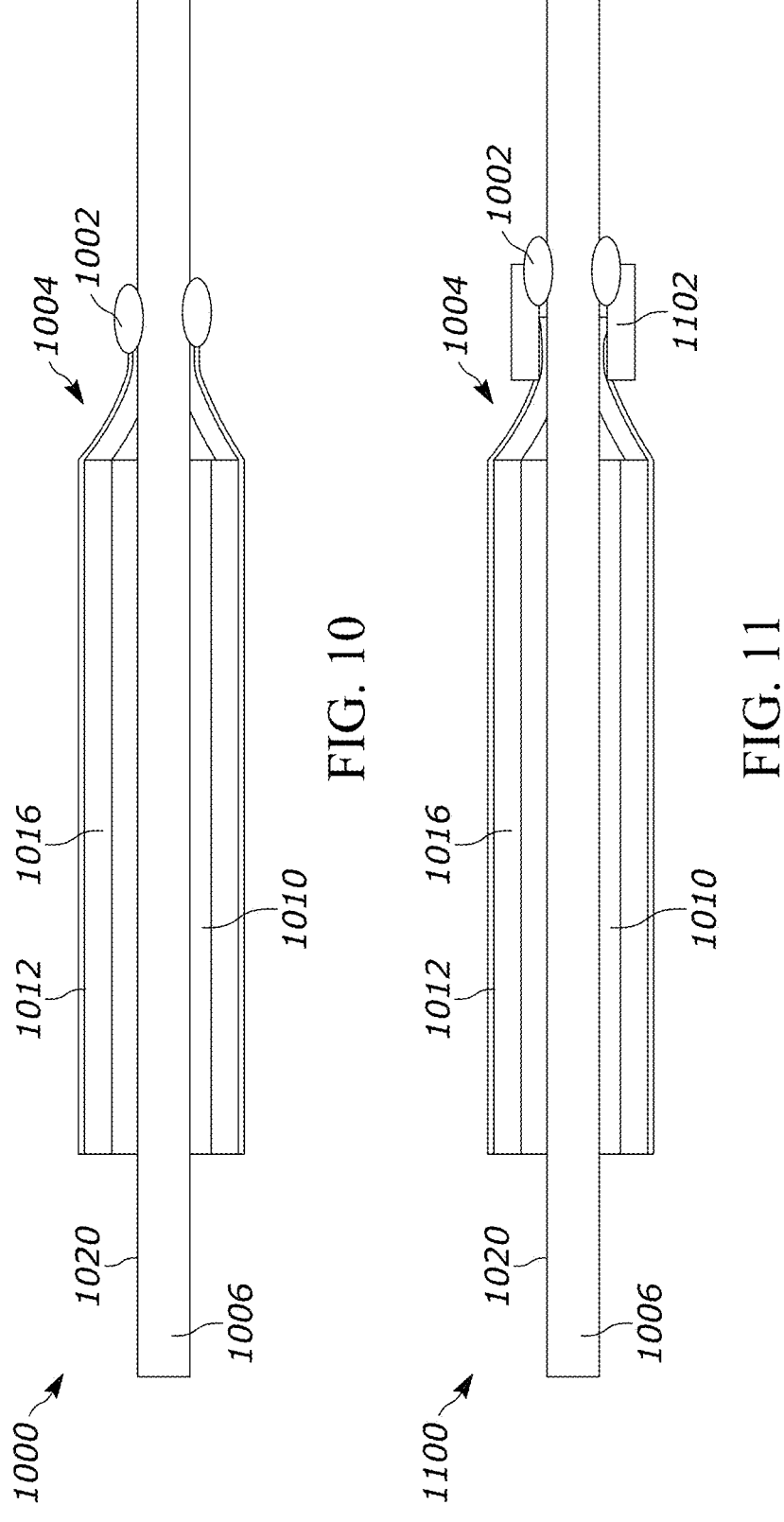

FLUID-COOLED LOW-PROFILE MICROWAVE ABLATION PROBE WITH SPHERICAL ABLATION ZONE

TECHNICAL FIELD

The disclosure relates to microwave ablation probes. More specifically, the disclosure relates to microwave ablation probes that are fluid-cooled and have a low profile and a choke for creation of spherical ablation zones.

BACKGROUND

Microwave ablation probes can be used in clinical treatments such as thermal ablation treatments. In such treatments, thermal ablation can be used to destroy undesirable tissue such as malignant cells in a body. A microwave ablation antenna can be included in the probe and be used to deliver Radio Frequency (RF) energy such as microwave energy to a target tissue to heat the target tissue and destroy the target tissue. The microwave ablation antenna can be positioned inside the ablation probe that can position the microwave ablation antenna proximate the target tissue.

In some treatments, the ablation probe is guided to the target tissue though other tissue or near to tissues or body structures that it is desirable not to damage during treatment. It is desirable, therefore, to maintain a small size of the microwave ablation antenna and/or the ablation probe. In this manner, damage to tissues and other body structures that may be located close to the target tissue to be destroyed is minimized or prevented. It is also desirable that the microwave ablation antenna produce a repeatable and known heating zone relative to the position of the microwave ablation antenna. The heating zone can then be reliably delivered to the target tissue without damaging or with minimized damage to surrounding tissue and body structures. There exists a need, therefore, for improved microwave ablation probes and/or antennas that have a sufficiently small size to prevent undesirable damage that can also reliably and repeatably produce known heating zones.

SUMMARY

The methods and apparatuses described herein are directed to embodiments and example ablation probes that can include a cooling system and a choke to produce an ablation zone having a desired size and shape. In some examples, the ablation probes of the present disclosure may include chokes positioned inside a cooling tube. The size and/or diameter of the cooling tube may vary at different axial positions relative to a tip of the probe.

In accordance with some embodiments, a microwave ablation probe is provided. The microwave ablation probe may include a cable extending in an axial direction that includes an antenna configured to deliver Radio Frequency (RF) energy. The probe may also include a shell positioned radially outward of the cable and defining a probe tip and a choke electrically coupled to an outer conductor of the cable. The probe may also include a cooling tube positioned inside the shell and positioned radially outward of the cable. The cooling tube including a first portion with a first outer diameter and a second portion with a second outer diameter. The second portion located radially outward of the choke and the second outer diameter being greater than the first outer diameter.

In one aspect, the first portion may be positioned at a longitudinal position away from the choke in a longitudinal direction away from the antenna.

In another aspect, the second portion is located closer to the probe tip than the first portion.

In another aspect, the first portion of the cooling tube may be a first length of tubing and the second portion of the cooling tube may be a second length of tubing. The first length of tubing and the second length of tubing may overlap at a joint.

In another aspect, the joint may be positioned at a longitudinal position adjacent the choke on a side away from the antenna.

In another aspect, the joint may be positioned adjacent the choke on a side away from the probe tip.

In another aspect, the first portion of the cooling tube and the second portion of the cooling tube can be connected by a transition having a conical shape.

In another aspect, the second portion is positioned radially outward of the antenna.

In another aspect, the cooling tube can be made of a non-metallic material.

In another aspect, the cooling tube can be made of a polymer material.

In another aspect, the cooling tube may include a rigid support tube that ends at a longitudinal position apart from the choke away from the antenna.

In another aspect, the cooling tube may include a rigid support tube that ends on a side of the choke away from the probe tip.

In another aspect, the shell may include a tip and a support tube. The tip including a composite material and the support tube comprising a stainless steel tube. The stainless steel tube may end at a longitudinal position away from the choke in a direction longitudinally away from the antenna.

In another aspect, the shell may include a shell end and a support tube, the shell end comprising a composite material and the support tube includes a stainless steel tube. The stainless steel tube ends at a side of the choke in a direction away from the probe tip.

In another aspect, the choke may include an outer conductor layer separated from the cable by an insulator layer.

In another aspect, the outer conductor layer includes a metal ink.

In another aspect, the outer conductor layer includes a metallic mesh material.

In another aspect, the insulator layer includes a polyimide ink material.

In some embodiments of the present disclosure, a microwave ablation probe may include a shell with a tip for insertion in a target tissue and a cable positioned inside the shell and configured to deliver microwave energy to an antenna. The probe may also include a choke coupled to the cable and a cooling tube positioned between the cable and the shell defining a cooling path for delivery of a cooling fluid, wherein the cooling tube varies in diameter.

In one aspect, the outer diameter of the shell is less than or equal to 2.1 mm.

In another aspect, the cooling tube has a larger diameter at a position at which the cooling tube extends over the choke.

In another aspect, an inner surface of the cooling tube defines a supply path for the cooling fluid and an outer surface of the cooling tube defines a return path for the cooling fluid. The choke may be positioned in the supply path.

In another aspect, the cooling tube includes two lengths of different diameter tubing joined together.

In another aspect, the cooling tube includes a continuous length of tubing with a conical transition between a first diameter portion to a second diameter portion.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The features and advantages of the present disclosures will be more fully disclosed in, or rendered apparent by the following detailed descriptions of example embodiments. The detailed descriptions of the example embodiments are to be considered together with the accompanying drawings wherein like numbers refer to like parts and further wherein:

FIG. 10 is a cross-sectional side view of a portion of an ablation probe illustrating another example choke in accordance with some embodiments of the present disclosure.

FIG. 11 is a cross-sectional side view of a portion of an ablation probe illustrating another example choke in accordance with some embodiments of the present disclosure.

DETAILED DESCRIPTION

Figures 1, 2:
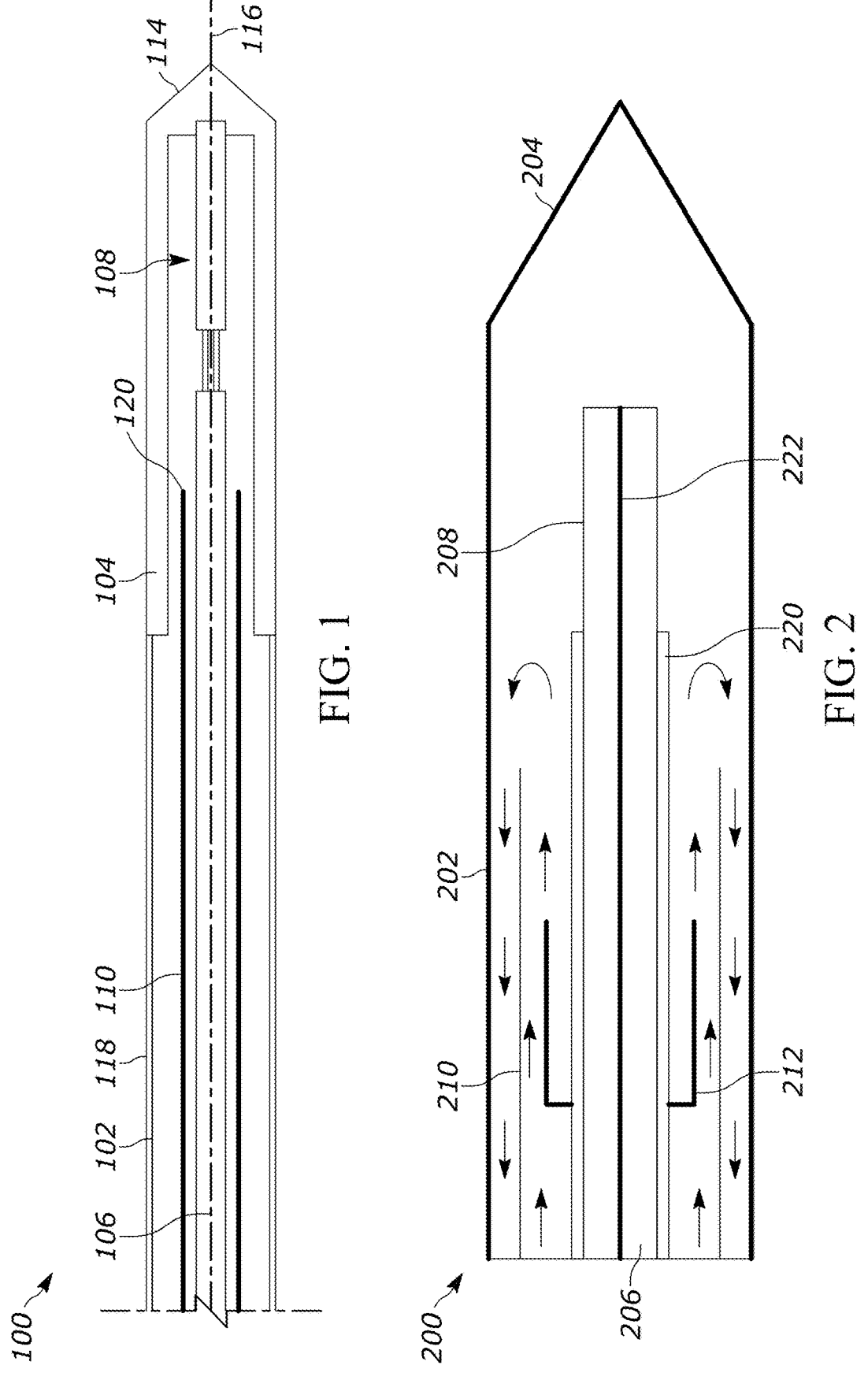
FIG. 1 is a cross-sectional side view of an example ablation probe illustrating aspects of some embodiments of the present disclosure.
FIG. 2 is a cross-sectional illustration of another example ablation probe illustrating aspects of some embodiments of the present disclosure.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The microwave ablation probes of the present disclosure can provide heating zones of a predictable and repeatable shape relative to the microwave ablation antenna. Existing probe and antenna configurations often produce elongated or teardrop-shaped heating zones around the antenna due to the unwanted backward or return current along the probe in a direction away from the antenna. Heating zones may also have undesirable elongated shapes in existing probe configurations due to thermal energy being transferred (e.g., conducted) along the probe. The elongated heating zones of existing probe and antenna designs are undesirable because the elongated heating zones can cause areas of body tissue to be heated and/or damaged that are not being targeted by the ablation treatment. In addition, portions of the probe may stick to the ablated tissue due to a heated surface of the probe. This condition can result in damage to tissue when the probe is retracted after the ablation procedure.

The ablation probes and antennas of the present disclosure can produce a heating zone that is more spherical in shape than existing probes and antennas. The ablation probes of the present disclosure do not heat in undesirable locations or produce the elongated or teardrop shaped heating zones. In this manner, the ablation probes and antennas of the present disclosure produce improved performance over existing designs. In addition, the probes of the present disclosure can maintain an overall profile that is smaller and/or has a smaller outer diameter that existing designs. These improvements over existing ablation probes produces more effective treatments by producing repeatable, spherical-shaped heating zones and reduced the likelihood of harm to healthy and non-targeted tissues.

Microwave ablation probes are often used during ablation treatments to target undesirable tissues such as tumors. During such procedures, the ablation probe can be inserted into a body and be positioned at or near the target tissue. The microwave ablation antenna included in the probe can emit radio frequency (RF) energy such as microwave energy. The microwave energy can be fed to the antenna via a feeding cable that couples a microwave generator to the antenna. The microwave energy can travel from the microwave generator to the antenna in the form of current.

In many examples, the feeding cable is a coaxial cable that can include an inner conductor and an outer conductor with an insulation in between. The current can travel from the microwave generator to the antenna on the surface of the cable inner conductor and the inner surface of the outer conductor. During a treatment procedure, the current on the inner conductor radiates into the target tissue heating the tissue. The current on the inner surface of the outer conductor can travel back (or can return) toward the microwave generator on the outer surface of the outer conductor of the feeding cable. This backward current can radiate tissues that may be located adjacent to or near the feeding cable. This condition can be undesirable because the radiation of energy can heat and/or damage tissues other than the target tissue that is targeted for the treatment.

Turning now to FIG. 1, an example ablation probe 100 is shown. The probe 100 may include a shell 102, an end portion 104, a cable 106, an antenna 108, and a cooling tube 110. The probe 100 may configured as an elongated cylindrical member that can be inserted into the target tissue of the patient. The probe 100 preferably has a low profile or small outer diameter such as the size of a needle. In some examples, the probe 100 has an outer diameter of less than or equal to 2.1 mm or a size no larger than the size of a 14 gauge needle.

The probe 100 may be elongated along a longitudinal direction extending in a direction generally parallel to a central axis of the probe 100. As will be described, the elements of the probe 100 are typically located concentrically about the central axis 116. The shell 102 may be configured as the outermost member of the probe 100. The shell 102 may be configured as a hollow tube that can be made of one or more materials joined together. An outer surface of the shell 102 can generally have a smooth surface to facilitate the insertion of the probe 100 into the target tissue. A tip 114 can be located at a proximal end of the probe 100 and have a point to further facilitate the insertion of the probe 100.

In some examples, the shell 102 can be made of multiple materials joined together. The shell 102, in the example shown, can include the body portion 118 and the end portion 104. The body portion 118 can be made of a stainless steel or other relatively rigid material to provide structure to the probe 100. The end portion 104 can be joined to the body portion 118 using suitable joining materials such as adhesive, epoxy or the like. The end portion 104 can be made of a non-conductive material such as a plastic, ceramic, composite or other non-metallic material. The end portion 104 is made of suitable non-conductive material so as to allow RF energy to be conveyed from the antenna 108 through the shell 102. The end portion 104 may, therefore, be located at a portion of the probe 100 at or near the antenna 108 which is typically located at or near the tip 114 of the probe 100.

The cable 106 may be positioned as the innermost element of the probe 100 and may be positioned in a center of the probe 100 along the central axis 116. The cable 106 is configured to deliver a suitable current from a microwave generator (not shown) to cause microwave energy (or other RF energy) to be emitted from the antenna 108. The cable 106 can be a coaxial cable that includes a center conductor and an outer conductor. The center conductor may be positioned at a central axis of the cable 106. The outer conductor may be separated from the inner conductor and be configured as a cylinder of conductive material positioned radially outward of the inner conductor along the length of the cable 106.

The antenna 108 may be positioned at a proximal end of the cable 106 at or near the tip 114 of the probe 100. The antenna 108 can be configured in any suitable manner such as monopole antenna or a dipole antenna. While one type or configuration of the antenna 108 may be shown in the figures, it should be appreciated that other types or configurations can also be used. As previously described, the antenna 108 is configured to emit RF or microwave energy to heat tissue that is located at or near the antenna 108. In this manner, the probe 100 can generate a heating zone that is generally located around the antenna 108 at or near the tip 114 of the probe 100.

When in use, the energy of the antenna and backward current along the outer conductor of the cable 106 may cause the probe 100 to increase in temperature. The heating of the probe 100 may cause the heating zone to become elongated in a longitudinal direction of the probe 100. The elongated heating zone may have an elliptical or teardrop shape, for example. In addition, if the exterior surface of the shell 102 increases in temperature, the tissue in contact with the shell 102 may stick to the shell 102. When the probe 100 is retracted after treatment, the tissue may tear resulting in tearing and/or bleeding that is undesirable. To prevent undesirable heating the probe and to maintain a more spherical heating zone shape, the probe 100 may include a cooling system to actively cool the probe 100 during operation.

In this example, the probe 100 includes the cooling tube 110. The cooling tube 110 can be located between the cable 106 and the shell 102. Thus, the cooling tube 110 can be located radially outward of the cable 106 and radially inward of the shell 102. The cooling tube 110 can be a cylindrical conduit made of a suitable metal (e.g., stainless steel) or other materials. The cooling tube 110 extends longitudinally into the probe 100 along the central axis 116 with a terminating end 120 of the cooling tube 110 being positioned at or near the antenna 108. In this arrangement, the cooling tube 110 does not surround or cover the antenna 108 and/or does not inhibit the antenna's ability to distribute RF energy. In other examples, the cooling tube 110 can be a non-metallic tube. In such examples, the cooling tube 110 may extend over and cover a large portion of the antenna 108. Such an arrange may improve radiation performance.

The cooling tube 110 is configured to deliver a cooling fluid toward the tip 114 of the probe 100. While not shown, the cooling system can include a source of cooling fluid and/or a suitable pump that can deliver a flow of cooling fluid in the interior of the cooling tube 110 toward the tip 114 of the probe 100. The cooling fluid may return to the source of the cooling fluid or be exhausted or otherwise deposited to another location. During operation, the cooling fluid can flow in a flow path in which the cooling fluid is delivered to the probe in an input channel defined by an interior surface of the cooling tube and an exterior surface of the cable 106. The cooling fluid may flow away from the tip 114 in a return channel defined by an exterior or outer surface of the cooling tube 110 and in interior surface of the shell 102. The flow of the cooling fluid may follow a path as indicated by the arrows shown in FIG. 2. In alternate examples, the cooling fluid may flow in a path opposite to that indicated in FIG. 2. In still other examples, the probe 100 can be cooled in either direction (i.e., in the direction shown by the arrows in FIG. 2 or in an opposite direction). The cooling fluid may be any suitable flowable cooling liquid or gas such as water, saline, carbon dioxide gas, or the like.

Referring now to FIG. 2, another example probe 200 is shown. The probe 200 may be similar in many respects to the probe 100 previously described. The probe 200 may include a shell 202, a cooling tube 210, and a cable 206. The cable 206 is positioned at a centralized position in the probe 200. The cable 206 includes an inner conductor 222 and an outer conductor 220. The cable 206 may include an antenna 208 that is configured to deliver RF energy and/or microwaves to a target tissue. The antenna 208 may be positioned proximate to a tip 204 of the probe 200.

In this example, the probe 200 may also include a choke 212. The choke 212 can be positioned radially outward of the cable 206 and radially inward of the cooling tube 210. In this position, the choke may be positioned between the cable and the cooling tube 210. The choke 212 may be positioned at a desired longitudinal location from the tip 204 and/or from the antenna 208 and be electrically coupled to the outer conductor 220 of the cable 206. In this manner, the choke 212 can limit the current that backflows along the outer conductor 220 when the probe is in operation. By limiting the current that flows back (i.e., in a direction away from the tip 204) along the outer conductor 220, the choke 212 can limit and/or reduce the generation of heat along the cable 206 and/or along the probe 200. The choke 212 can reduce the likelihood that that the heating zone that is produced during operation of the probe 200 has an elongated, elliptical or teardrop shape. The choke 212 can assist in producing a more spherical and/or symmetric heating zone around the tip 204 of the probe 200.

The choke 212 can have various configurations and can be made of various materials. FIGS. 3-17 illustrate various configurations of chokes that can be used in the probes of the present disclosure. The illustrated configurations of FIGS. 3-17 do not include all the aspects of the probes 100, 200 previously described. It should be understood that the chokes illustrated and described can be used in the probes 100, 200 and in any of the other probes described in the present disclosure.

Figures 3, 4, 5:
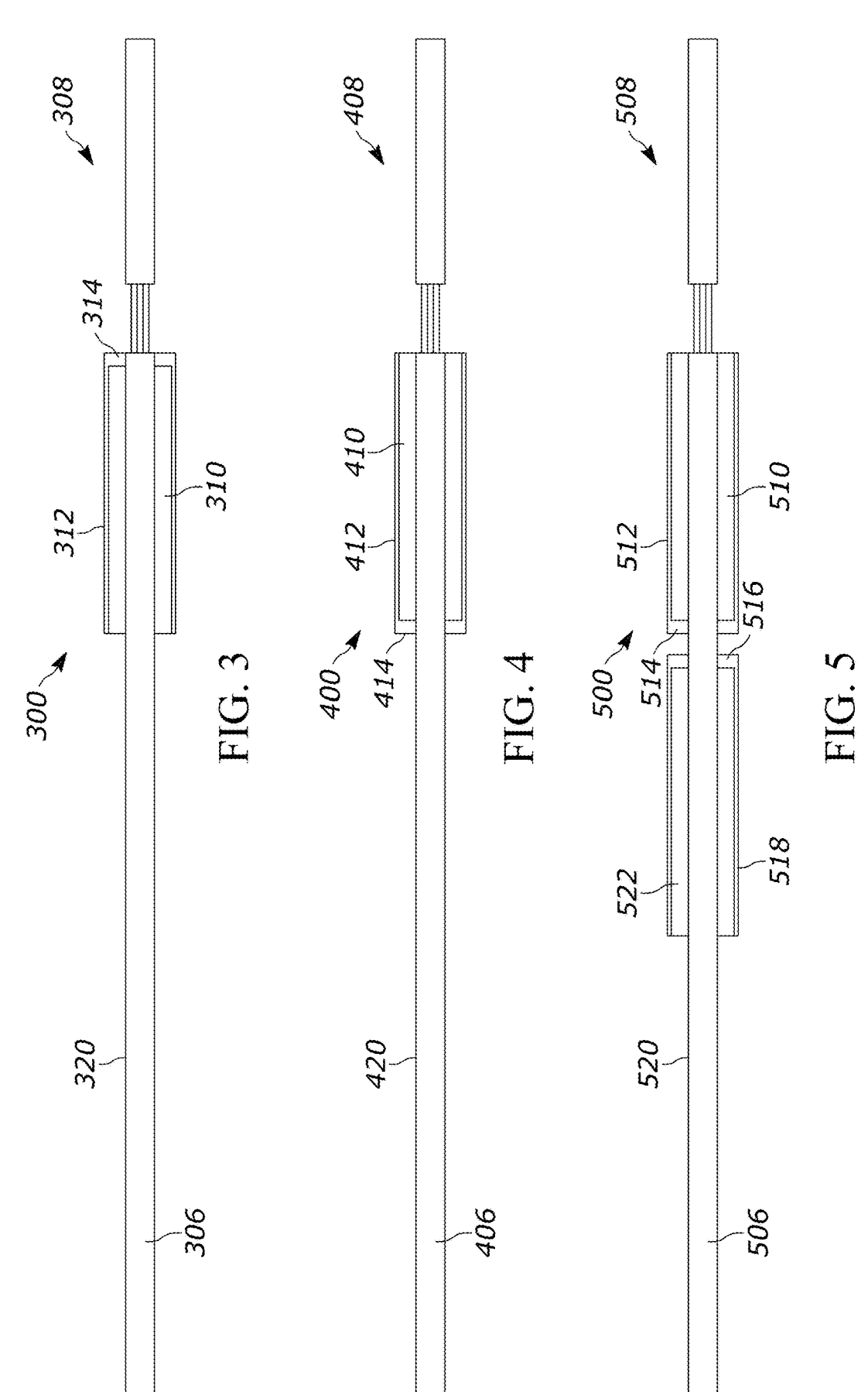
FIG. 3 is a cross-sectional side view of a portion of an ablation probe illustrating an example choke in accordance with some embodiments of the present disclosure.
FIG. 4 is a cross-sectional side view of a portion of an ablation probe illustrating another example choke in accordance with some embodiments of the present disclosure.
FIG. 5 is a cross-sectional side view of a portion of an ablation probe illustrating another example choke in accordance with some embodiments of the present disclosure.

As shown in FIG. 3, an example choke 300 may include a conductor 312 and an insulator 310. The choke 300 may be positioned at a desired location relative to the antenna 308. A connection portion 314 may couple the choke 300 to the outer conductor 320 of the cable 306. The choke 300 may be configured as a cylindrically shaped member that surrounds the cable 306. The conductor 312 can be separated from the cable 306 in the longitudinal direction along an axis of the cable 306. The conductor 312 can be formed of a suitable conductive metal material such as stainless steel, copper, or other metal or alloy. The insulator 310 can be formed of a suitable insulating material such as a polymer, perylene, polytetrafluoroethylene (PTFE), polyimide, epoxy, or the like. The connection portion 314 may be soldered, crimped or otherwise connected to the cable 306.

Another example choke 400 is shown in FIG. 4. The choke 400 may be similar to the choke 300 previously described. The choke 400 may include a conductor 412 and an insulator 410. The choke 400 may be positioned at a desired location relative to the antenna 408. A connection portion 414 may couple the choke 400 to the outer conductor 420 of the cable 406. In this example, the connection portion 414 is positioned on a side of the choke away from the antenna 408. This differs from the configuration shown in FIG. 3. The choke 400 may be configured as a cylindrically shaped member that surrounds the cable 406. The insulator 410 and the conductor 412 may be made similarly to that described above for choke 300.

Another choke configuration 500 is shown in FIG. 5. In this example, the choke 500 includes a first choke portion that is made of a first conductor 512, a first insulator 510, and a first connection portion 514. The choke 500 also includes a second portion with a second conductor 518, a second insulator 522, and a second connection portion 516. The first connection portion 514 and the second connection portion 516 are positioned adjacent one another on outer conductor 520 of the cable 506. The first choke portion and the second choke portion can be configured similarly to the choke 300 and/or choke 400 previously described.

Figures 6, 7, 8:
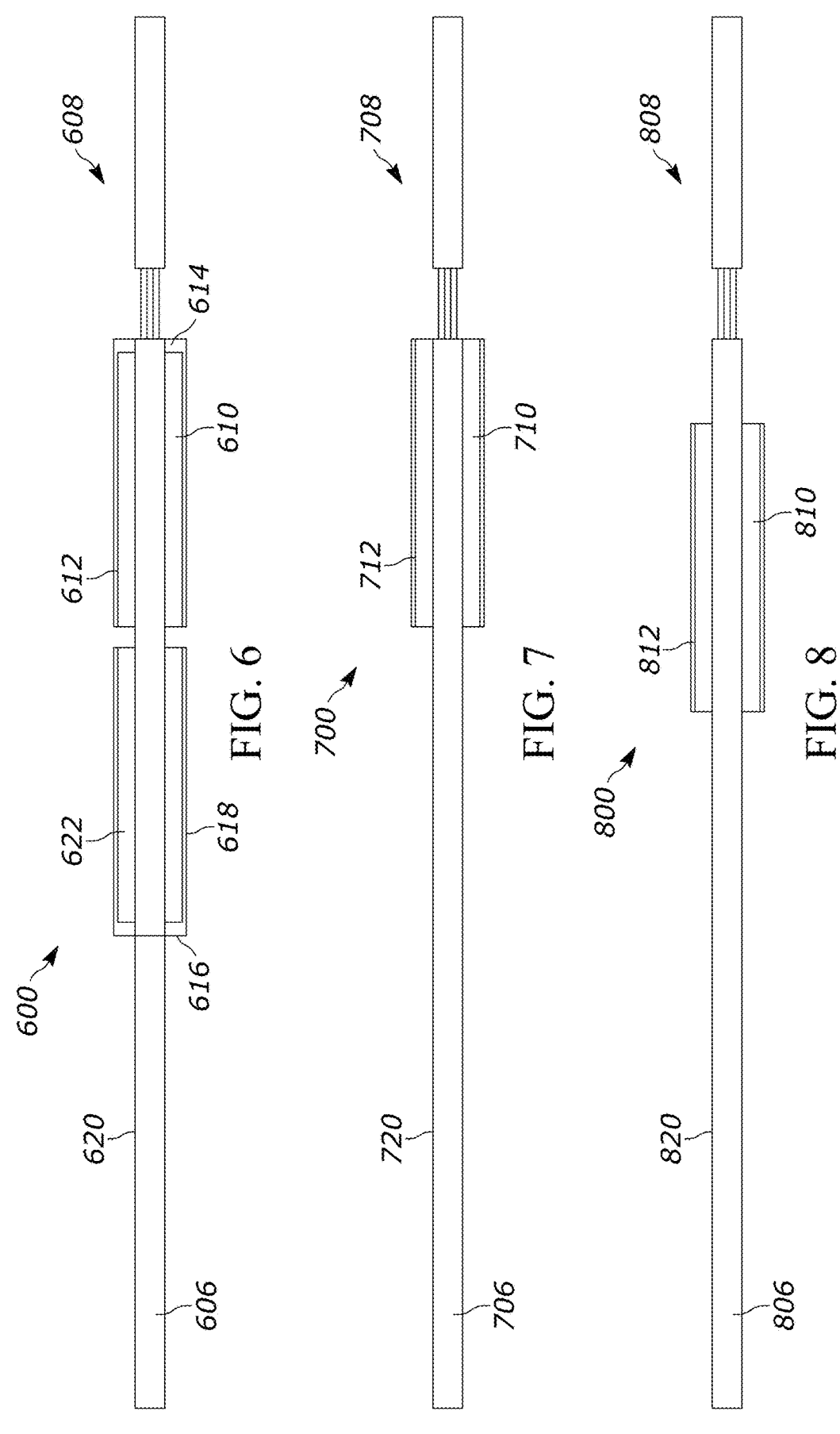
FIG. 6 is a cross-sectional side view of a portion of an ablation probe illustrating another example choke in accordance with some embodiments of the present disclosure.
FIG. 7 is a cross-sectional side view of a portion of an ablation probe illustrating another example choke in accordance with some embodiments of the present disclosure.
FIG. 8 is a cross-sectional side view of a portion of an ablation probe illustrating another example choke in accordance with some embodiments of the present disclosure.

Another choke configuration 600 is shown in FIG. 6. The choke 600 in this example includes a first choke portion and a second choke portion similarly to the choke 500. The first choke portion includes a first conductor 612, a first insulator 610, and a first connection portion 614. The second choke portion includes a second conductor 618, a second insulator 622, and a second connection portion 616. In this example, the first connection portion 614 is positioned at a first end of the choke 600 proximate the antenna 608. The second connection portion 616 is positioned at an end opposite the first connection portion 614. The elements of the choke 600 can be made of similar materials to that previously described with respect to choke 300, 400.

Another choke variation is shown in FIG. 7. In this example, choke 700 includes conductor 712 and insulator 710. The choke 700 is positioned at a predetermined longitudinal distance from the antenna 708. The choke 700 an be positioned along the cable 706 and connected to the outer conductor 720 using various suitable connections.

Another choke variation is shown in FIG. 8. In this example, choke 800 includes conductor 812 and insulator 810. The choke 800 is positioned at a predetermined longitudinal distance from the antenna 808. The choke 800 can be positioned along the cable 806 and connected to the outer conductor 820 using various suitable connections. As compared to choke 700, choke 800 is positioned at a longitudinal distance further from the antenna 808 than the choke 700. Such distance may be chosen, for example, to cause the heating zone that is produced by the probe to have a desired shape.

Figures 9A, 9B, 9C:
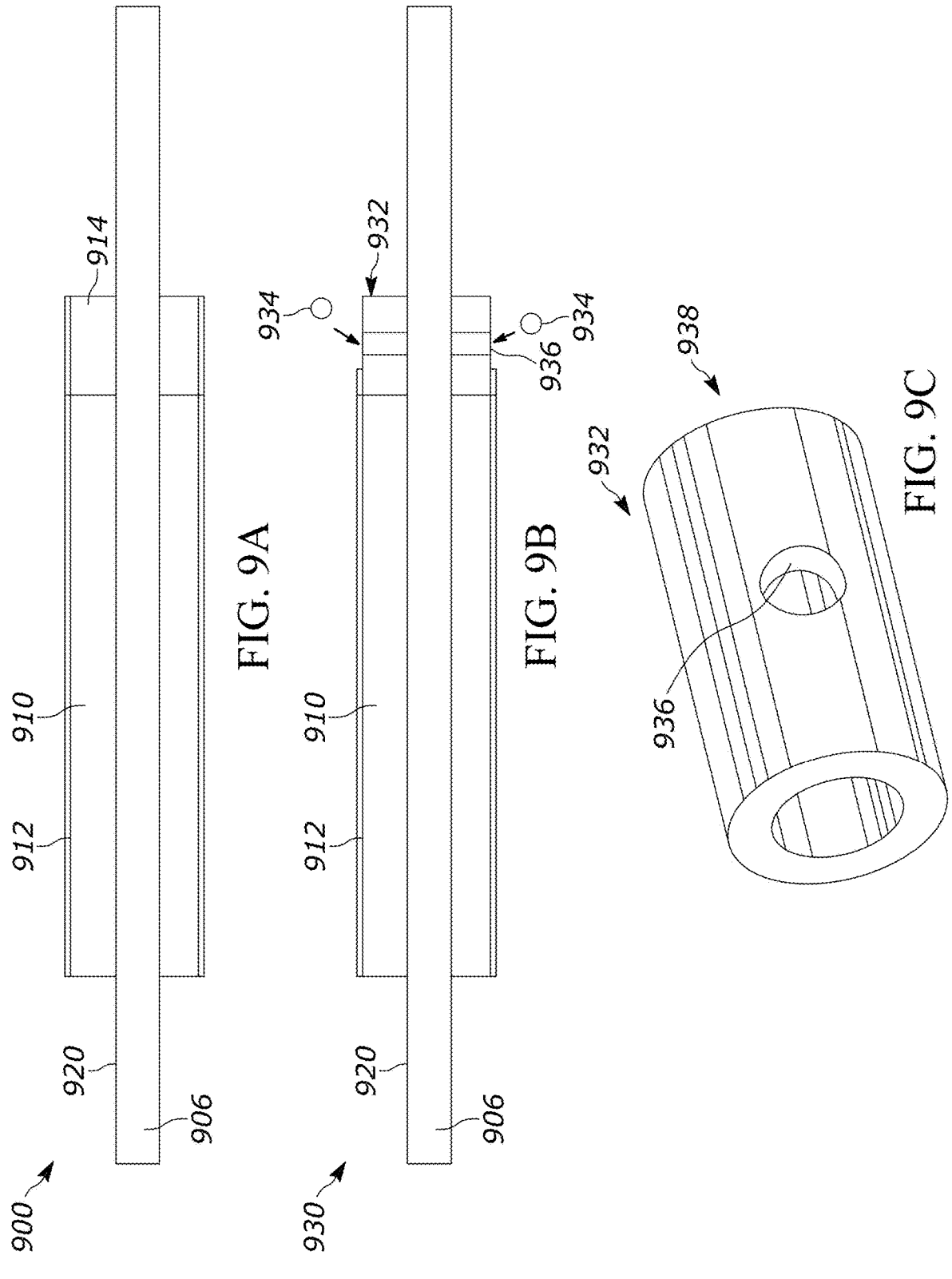
FIG. 9A is a cross-sectional side view of a portion of an ablation probe illustrating another example choke in accordance with some embodiments of the present disclosure.
FIG. 9B is a cross-sectional side view of a portion of an ablation probe illustrating another example choke in accordance with some embodiments of the present disclosure.
FIG. 9C is an isometric view of an example disc that may be used in the choke of FIG. 9B.

Another choke variation is shown in FIG. 9A. The choke 900, in this example, includes a conductor 912, an insulator 910 and a connection disc 914. The choke 900 can be positioned on the cable 906 to reduce and/or limit current from traveling away from the antenna (not shown) and back down the outer conductor 920 of the cable 906. In this example, the conductor 912 may be a metal coating and the insulator 910 may be a suitable insulating material such as polyetheretherketone (PEEK) or polyethylene terephthalate (PET). The connection disc 914 can be made of a brass, copper or other suitable metal or alloy. In other examples, other materials can be used. The connection disc 914 may have an annular shape and be positioned to couple the outer conductor of the cable 906 to the conductor 912.

Another choke variation is shown in FIG. 9B. The choke 930 may be similar to the choke 900 previously described. The choke 930 includes the conductor 912, the insulator 910 and a connection disc 932. The connection disc 932 in this example may include one or more openings 936 that extends through the body of the disc 932 from an external surface to an internal surface of the disc 932 as shown in FIG. 9C. The disc 932 can be tubular or annular in shape with a central opening 938. The disc 932 can be positioned over the cable 906 with the opening 936 extending from the exterior of the disc 932 to the cable 906. One or more beads or spheres of solder 934 can be positioned in each of the openings 936 to solder the disc in position to electrically couple the disc to the conductor 912 and/or to the cable 906. The beads of solder 934 can be of a predetermined diameter, weight, volume or other size such that the amount of solder is accurately controlled to prevent undesirable short circuit conditions and/or gapping conditions. In the example shown, the disc 932 includes two opposing openings 936 each positioned on opposite sides of the disc 932. In other examples, other numbers of openings 936 and beads of solder 934 can be used.

Another choke variation is shown in FIG. 10. In this example, the choke 1000 may include an outer surface 1012 that is coupled to a metalized heat shrink material 1016. Radially inward of the metalized heat shrink material 1016, an insulator 1010 may be positioned adjacent the cable 1006. The insulator 1010 may be made of a suitable polymer, polytetrafluoroethylene (PTFE), or other insulating material. The choke 1000 may include a connection zone 1004 that may be formed by the metalized heat shrink material 1016 being crimped, heat shrunk, or otherwise compressed to contact the cable 1006. A solder 1002 can be deposited at the connection zone 1004 to ensure connection between the conductor 1012 and the cable 1006.

Another choke variation 1100 is shown in FIG. 11. The choke 1100 may be similar to the choke 1000 previously described. The choke 1100 in this example may additionally include a supplemental connector 1102. The supplemental connector may be a hollow cylindrical member or annular member sized to fit over the cable 1006 and over the connection zone 1004. The supplemental connector 1102 can be made of a copper, brass, or other suitable conductive metal or alloy. Solder 1002 can also be used to ensure connection between the conductor 1012 and the cable 1006.

Figures 12, 13, 14:
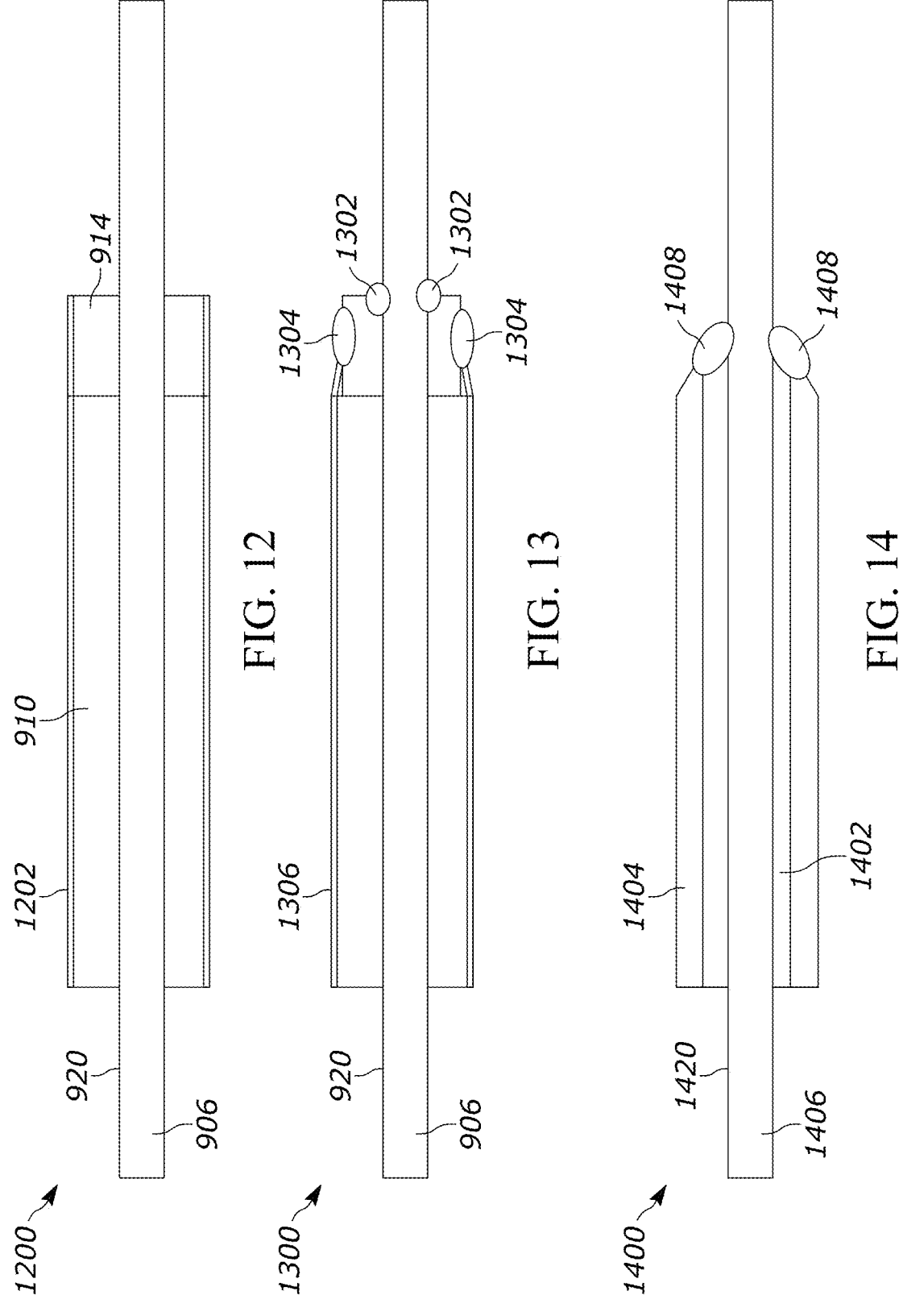
FIG. 12 is a cross-sectional side view of a portion of an ablation probe illustrating another example choke in accordance with some embodiments of the present disclosure.
FIG. 13 is a cross-sectional side view of a portion of an ablation probe illustrating another example choke in accordance with some embodiments of the present disclosure.
FIG. 14 is a cross-sectional side view of a portion of an ablation probe illustrating another example choke in accordance with some embodiments of the present disclosure.

Still another choke variation 1200 is shown in FIG. 12. In this example, the choke 1200 may be configured and constructed similarly to the choke 900 previously described. In this example, the outer conductor 1202 of the choke 1200 may be formed of metal ink. A metal conductive ink can be printed or otherwise deposited on the external surface of the choke 1200 to form the conductor 1202. The conductive metal ink can be coupled to the connector disc 914 and, in turn, to the cable 906.

Another choke variation 1300 is shown in FIG. 13. In this example, the choke 1300 may be similar to the choke 900 previously described. In this example, the conductor 1306 may be formed of a copper foil material. The copper foil material of the conductor 1306 can be coupled to the connector disc 914 using a suitable solder pattern that include solder points 1304 to connect the copper foil to the connector disc 914 and solder points 1302 to connect the connector disc 914 to the outer conductor 920 of the cable 906. In other examples, other crimps, materials and features can also be used to ensure or improve the electrical connection of the copper foil to the cable 906.

Another example choke 1400 is shown in FIG. 14. In this example, the choke 1400 may include an outer conductive layer 1404 and an inner insulator layer 1402. The conductive layer 1404 can be made of various conductive materials such as stainless steel or the like. The conductive layer 1404 can be formed from a length of stainless steel tubing, for example. The insulator layer 1402 can be made of various insulating materials and in one example, is formed of perylene. The perylene or other insulator layer can be formed or deposited as a layer or coating on the inner surface of the stainless steel tubing. Solder 1408 can be deposited at one end of the choke 1400 to connect the conductive layer 1404 to the cable 1406.

Figures 15, 16, 17:
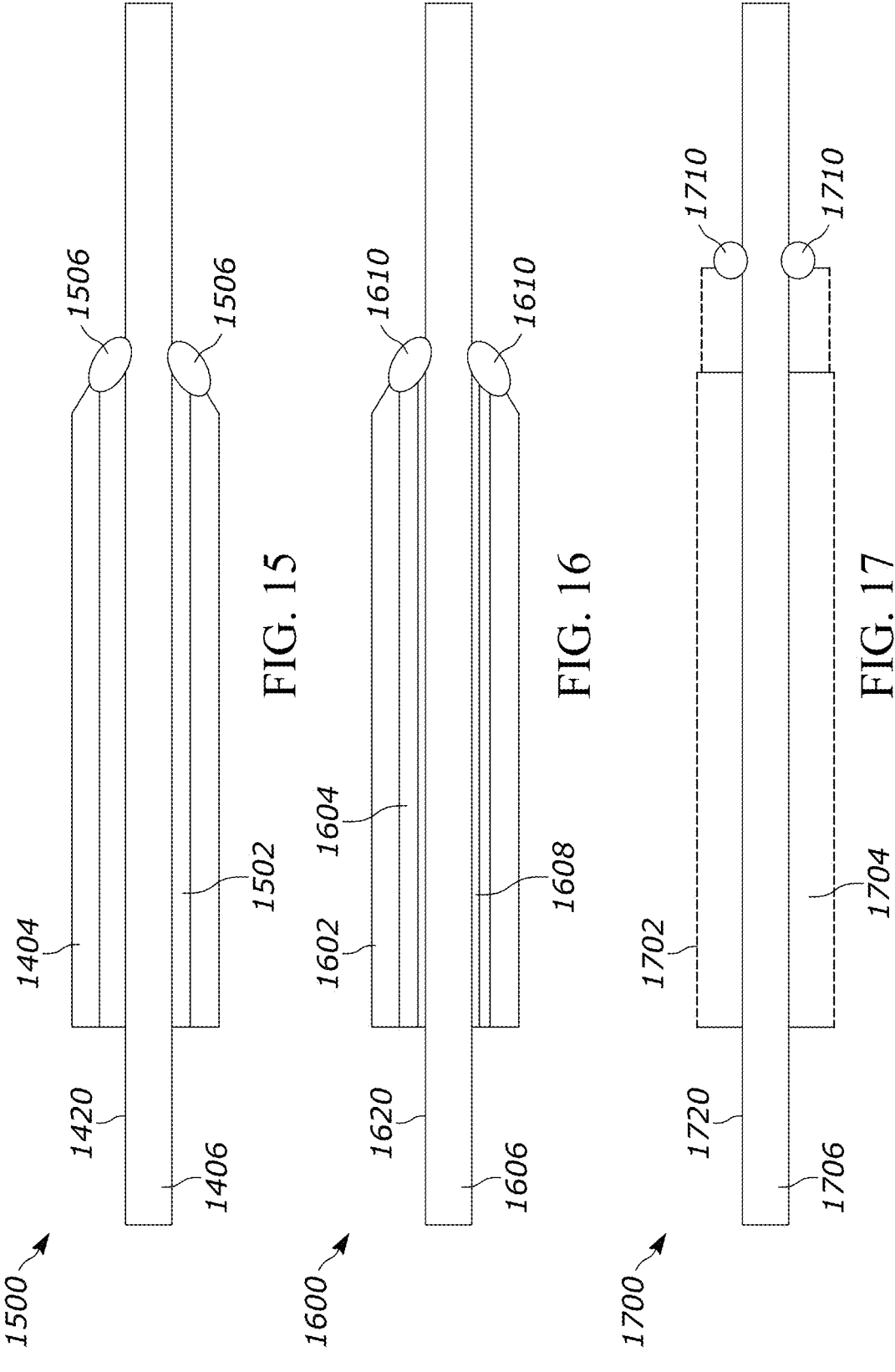
FIG. 15 is a cross-sectional side view of a portion of an ablation probe illustrating another example choke in accordance with some embodiments of the present disclosure.
FIG. 16 is a cross-sectional side view of a portion of an ablation probe illustrating another example choke in accordance with some embodiments of the present disclosure.
FIG. 17 is a cross-sectional side view of a portion of an ablation probe illustrating another example choke in accordance with some embodiments of the present disclosure.

Another example choke 1500 is shown in FIG. 15. In this example, the choke 1500 may be similar to the choke 1400 previously described. In this example, however, the insulator layer 1502 may be formed of a ultra violet (UV) and/or heat cured epoxy. The conductive layer 1404 can be made of various conductive materials such as stainless steel or the like. The conductive layer 1404 can be formed from a length of stainless steel tubing, for example. The choke 1500 may be assembled, for example, by placing the insulator layer 1502 on the cable 1406 or by placing the insulator layer 1502 in the tubing of the conductive layer 1404. The tubing 1404 can then be positioned over the cable 1406 in the desired position. In other examples, the tubing 1404 can be placed in a desired position and the UV and/or heat cured epoxy can be wicked into the space between the tubing 1404 and the outer conductor 1420 of the cable 1406. The insulator layer 1502 can be cured to a secured state by subjecting the cured epoxy to UV light and/or a heat source. The insulator layer 1502 can become cured as a result securing the tubing 1404 in position and acting as an insulator between the outer conductor 1420 of the cable 1406 and the tubing 1404. Solder 1506 can then be deposited on an end of the choke 1500 to electrically couple the outer conductor 1420 of the cable 1406 to the conductor layer 1404.

Another example choke 1600 is shown in FIG. 16. In this example, the choke 1600 may include a conductor layer 1602, a first insulating layer 1604, and a second insulating layer 1608. The first insulating layer 1604 and the second insulating layer 1608 may be positioned between the conductor layer 1602 and the outer conductor 1620 of the cable 1606. In one example, the conductor layer 1602 may be made of a length of stainless steel or other metallic tubing. The first insulating layer 1604 may be formed of an insulating ink such as a polyimide nano ink. The second insulating layer 1608 may be formed of a length of polyimide tubing. In other examples, insulating layers 1604, 1608 can be formed of different insulating materials. The insulating layers 1604 and/or 1608 can be deposited onto the cable 1606 and then the conductor layer 1602 can be positioned over the insulating layers. Solder 1610 may be deposited on the choke 1600 to electrically couple the conductor layer 1602 to the outer conductor 1620 of the cable 1606.

Another example choke 1700 is shown in FIG. 17. In this example, choke 1700 may include a mesh conductor layer 1702, an insulator layer 1704, and a connector 1708. The mesh conductor layer 1702 may be a woven or mesh of a conductive metal material. The mesh conductor layer 1702, for example, can be made of a braided, woven metal material often used for stents or the like. The insulating material can be used to form the insulator layer 1704 radially inward of the conductor layer 1702. The insulating material can be a polymer or PEEK material, for example. Connector 1708 can be positioned at one end of the choke 1700 and contact the conductor layer 1702 and the outer conductor 1720 of the cable 1706. Solder 1710 can be deposited to couple the outer conductor 1702 to the connector 1708 and to fix the choke 1700 in a desired position.

The chokes previously described can be used in the probes of the present disclosure to reduce or limit the current that travels back away from the antenna along the outer conductor of the cable. While each of the examples includes one choke, multiple of the same chokes can be used as well as combinations of different variations previously described.

As shown, the chokes include structures that are positioned over the cable that deliver the RF or microwave signal to the antenna. In such a position, the choke may be positioned radially outward of the cable that delivers the RF current to the antenna but radially inward of the cooling tube that delivers the cooling fluid to the probe. As can be appreciated, the cooling fluid may follow a path that in which it flows through the cooling tube, over and/or around the choke before reaching the end of the cooling tube and returning in a direction away from the antenna over an external surface of the cooling tube (see FIG. 2, for example). The cooling tube can be operated at a desired pressure, flow rate, temperature and other operating parameters to achieve a desired level of cooling in the probe. When the cooling fluid encounters a restriction in the size of the flow path, such as when the cooling fluid encounters the choke in the cooling path, such restriction may cause back pressure in the flow path. Such restriction on the flow of the cooling fluid may cause undesirable limitations on the ability of the cooling fluid to cool the probe as desired.

To address this problem, the probes of the present disclosure may include a cooling tube that includes different cross-sectional flow paths at different locations in the probe. For example, the cooling tube may include a first cross-sectional flow area at a first longitudinal position and a second cross-sectional flow area at a second longitudinal position. The second longitudinal position may correspond to a location of the choke. The corresponding second cross-sectional flow area at the choke may be larger than the cross-sectional flow area at the first longitudinal position located upstream or at a position further away from the distal end of the probe than the choke.

Figures 18, 19:
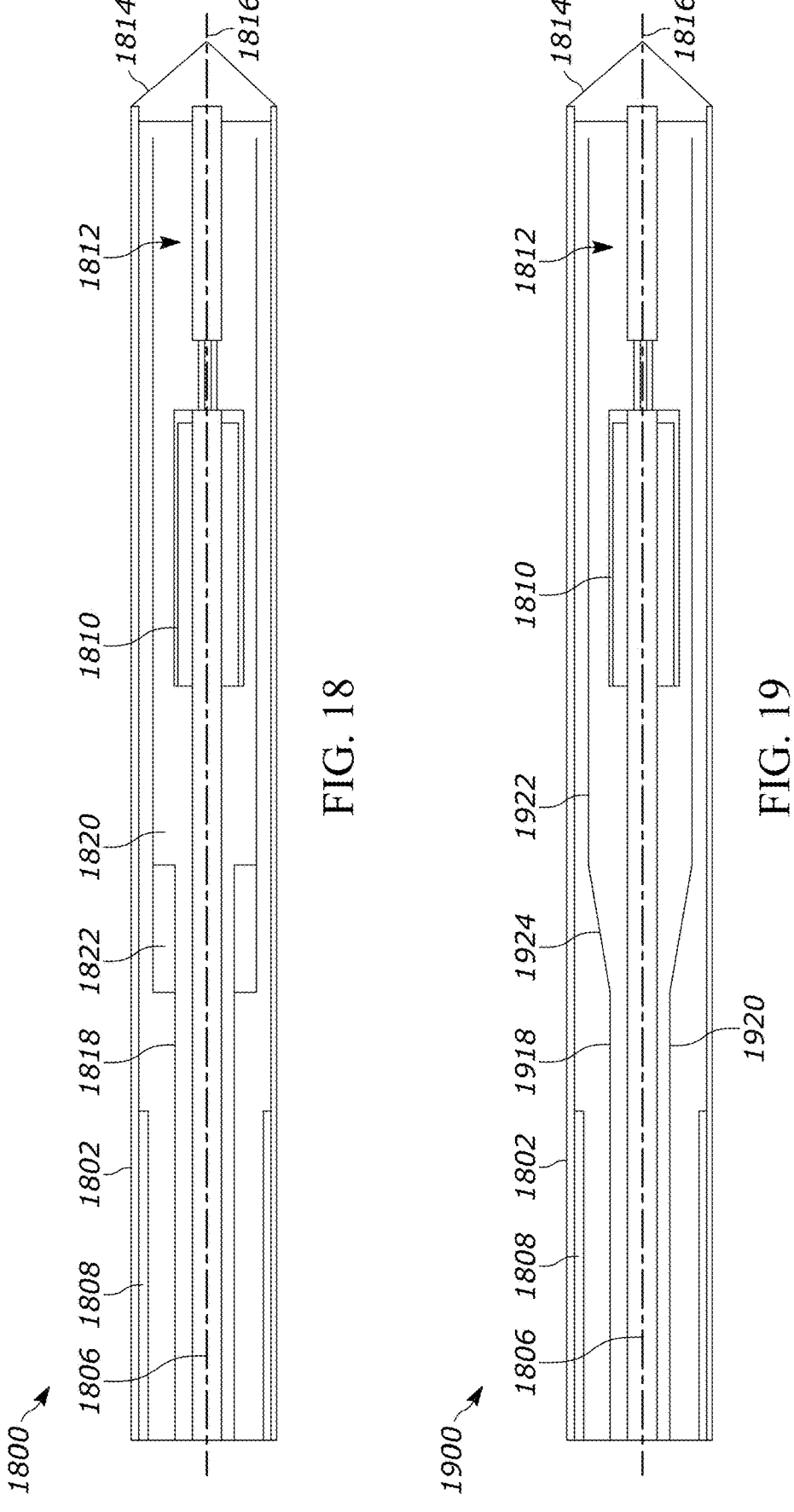
FIG. 18 is a cross-sectional side view of an example ablation probe in accordance with some embodiments of the present disclosure.
FIG. 19 is a cross-sectional side view of another example ablation probe in accordance with some embodiments of the present disclosure.

One example is shown in FIG. 18. In this example, the probe 1800 may include a shell 1802, a support tube 1808, a cable 1806, a choke 1810 and an antenna 1812. The probe 1800 may be similar to the probes previously described. The probe 1800 extends generally in a longitudinal direction along a central axis 1816. The cable 1806 can operate to deliver a suitable current to the antenna 1812 to generate microwave radiation that is delivered to a target tissue during an ablation treatment. The probe may also include a cooling tube positioned radially outward of the cable 1806 and the choke 1810. The cooling tube can include a first portion 1818 that is joined to a second portion 1820 at a joint 1822. The outer diameter of the first portion 1818 is smaller than the second portion 1820. Unlike other probes, the cooling tube in this example probe 1800 includes a cooling tube with a larger diameter at the choke to reduce the likelihood of back pressure or flow restriction at the choke 1810.

The shell 1802 of the probe 1800 may be made of a ceramic, fiberglass or other non-metallic material. Such non-conductive material is desired at the tip of the probe 1800 so as not to interfere or restrict the delivery of RF energy or microwaves to the target tissue from the antenna 1812. The probe may include a support tube 1808 that can be made of stainless steel or other rigid material to increase the rigidity of the probe 1800. Such support member 1808 stops before reaching a longitudinal position at or near the antenna 1812.

The cooling tube can be constructed of various suitable materials but is made of a non-metallic or non-conductive material since the cooling tube extends over the cable 1806 and over at least a portion of the antenna 1812. In one example, the first portion 1818 and the second portion 1820 can be made of a polyimide tubing. The first portion 1818 and the second portion 1820 can be made of other polymers or other materials as well. The first portion 1818 and the second portion 1820 can be made of the same material or different materials. In some examples, the first portion 1818 may be made of a conductive or metallic material and the second portion 1820 can be made of non-conductive material. The second portion 1820 includes an outer diameter and inner diameter larger than the first portion 1818. The second portion 1820 can be positioned over the first portion 1818 and secured using a suitable joint material such as an adhesive, epoxy, or the like. The second portion 1820 can be located at a longitudinal position that is closer to the distal end or tip 1814 than the first portion 1818.

The second portion 1820 can be located at a longitudinal position such that the second portion 1820 does not longitudinally overlap with the support tube 1808. In such a position, there is increased space inside the shell 1802. Thus, the larger diameter second portion 1820 does not cause or necessitate that the outer diameter of the shell 1802 be increased. As such, the outer diameter of the shell can be maintained to have an outer diameter no larger than about 2.1 mm and/or the size of a 14 gauge needle.

In another example shown in FIG. 19, a probe 1900 may also include a cooling tube that has a varying diameter at different portions along the longitudinal length of the probe. The probe 1900 may be similar to the probe 1800 previously described. The probe 1900 includes a shell 1802, a support tube 1808, a choke 1810 and an antenna 1812. The probe 1900 may be cylindrical and extend longitudinally along the center axis 1816. In this example, the cooling tube includes a first portion 1918 and a second portion 1922. The second portion 1922 can be located at a longitudinal position that is closer to the distal end or tip 1814 than the first portion 1918. The cooling tube includes a transition region 1924 that can be generally conical in shape and can transition from a first diameter at the first portion 1918 to a larger diameter at the second portion 1922. The transition region 1924 can be positioned at a longitudinal position after the support tube 1808 ends so as to permit the cooling tube to expand generally outward to have a larger diameter at the choke 1810. As with the probe 1800, the probe 1900 does not need to be expanded radially outward at the choke and can be formed to have an outer diameter that is no larger than about 2.1 mm and/or the size of a 14 gauge needle.

The cooling tube can be formed from a suitable polyimide or other non-conductive material. The cooling tube can be formed to from a continuous piece of material to have the shape as shown or can be formed from multiple pieces joined together. The transition region 1924, in this example, forms a smooth expansion of the cooling tube upstream of the choke 1810. This may prevent undesirable back pressure or flow restrictions at the choke 1810. Thus, stable cooling can be achieved during operation.

While not described again for the sake of brevity, the choke 1810 may be configured in any manner described in the present disclosure, including the example chokes of FIGS. 3-17. In addition, while one choke 1810 is shown in the examples, multiple chokes and various positions of the choke can also be used.

Figures 20, 21:
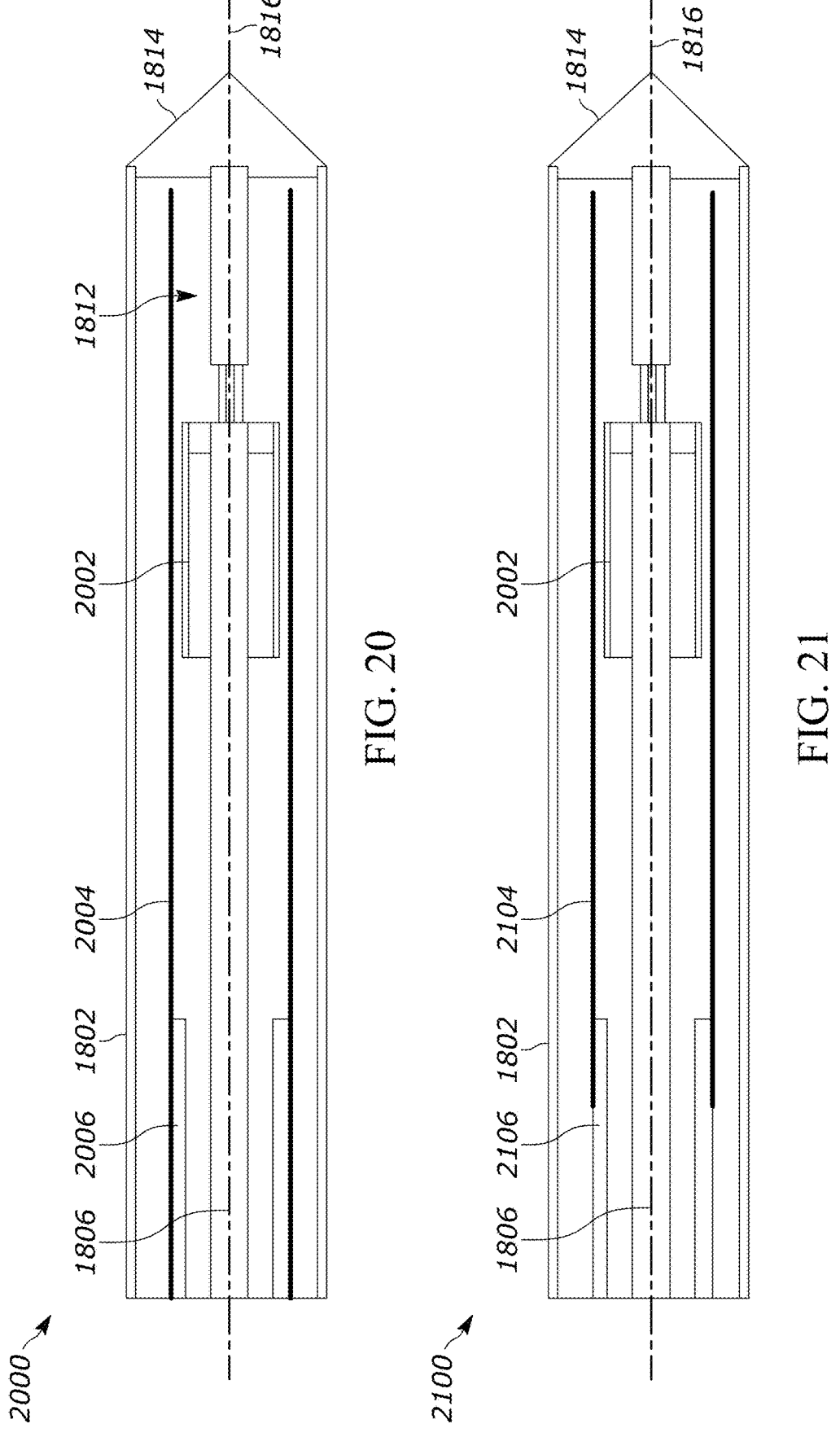
FIG. 20 is a cross-sectional side view of another example ablation probe in accordance with some embodiments of the present disclosure.
FIG. 21 is a cross-sectional side view of another example ablation probe in accordance with some embodiments of the present disclosure.

Referring now to FIGS. 20 and 21, example probes 2000 and 2100 are shown. The probes 2000, 2100 are similar in many aspects. As shown, each of the probes 2000, 2100 extend in a longitudinal direction along a central axis 1816. The probes 2000, 2100 include a cable 1806 positioned at a center along the central axis 1816. The cable 1806 is configured to deliver a current to the antenna 182 that can deliver RF energy or microwaves to the target tissue during an ablation treatment. The choke 2002 can be positioned before the antenna 1812 along the cable 1806 to limit and/or reduce the flow of current back along the cable 1806.

The probe 2000 also includes a cooling tube 2004 that is positioned inside the shell 1802 of the probe 2000. As shown, the cooling tube 2004 extends longitudinally over the choke 2002 and the antenna 1812. As such, the cooling tube 2004 is made of a non-conductive and/or non-metallic material so as to not interfere with the delivery of microwaves from the antenna 1812. In some examples a polyimide or other polymer material can be used. The rigidity of such material can be limited. To improve the rigidity of the probe 2000, a cooling support 2006 can be added along a portion of the longitudinal length of the probe 2000. In this example, the support 2006 can be made of stainless steel tubing or other rigid material and be positioned inside the cooling tube 2004.

The example probe 2100 is similar to the probe 2000. In this example, the cooling tube is constructed of a stainless steel or other rigid tube 2106 that extends along the probe 2100. The rigid portion 2106 stop at a position spaced away from the choke 2002 and the antenna 1812. A non-conductive or non-metallic portion 2104 is joined to the rigid tube 2106. In this example, the non-metallic portion 2104 is positioned such that it overlaps on the exterior of a portion of the rigid tube 2106. In other examples, the non-metallic portion 2104 can be positioned inside the rigid tube 2106.

While not shown in the examples 2000, 2100, the cooling tubes of the respective probes can include variable diameters in longitudinal positions upstream of the choke 2002 and at the choke 2002 as previously described. The cooling tube 2004, for example, may have different diameters as shown in FIG. 18 or 19. Similarly, the non-metallic portion 2104 of the cooling tube of probe 2100 may have different diameters and/or the shapes and structures as shown in FIGS. 18 and 19. In the context of the present disclosure the terms downstream and/or upstream are used to describe a direction of the cooling flow in the conduit or flow path being described. For example, since the choke 2002 can be positioned inside the cooling tube 2004, the upstream direction corresponds to a general direction away from the distal end or tip 1814 of the probe. Similarly, the term downstream, in this example, corresponds to a direction generally toward the distal end or tip 1814.

One of the advantages of the probes of the present disclosure is that the probes can be used to produce a more spherical and/or symmetric heating zone than existing or traditional probes. For the reasons previously stated, existing probes may produce an elongated, elliptical, or teardrop shaped heating zone that is often elongated in a direction along the probe away from the tip. The active cooling can allow less heating to occur along the probe. Furthermore, the structure of the choke and the cooling tube, as previously described, allows the probes of the present disclosure to have a low profile. Such low profiles allow the overall outer diameters of the probes to be smaller than other probes that may include cooling tubes and/or chokes.

Figures 22, 23:
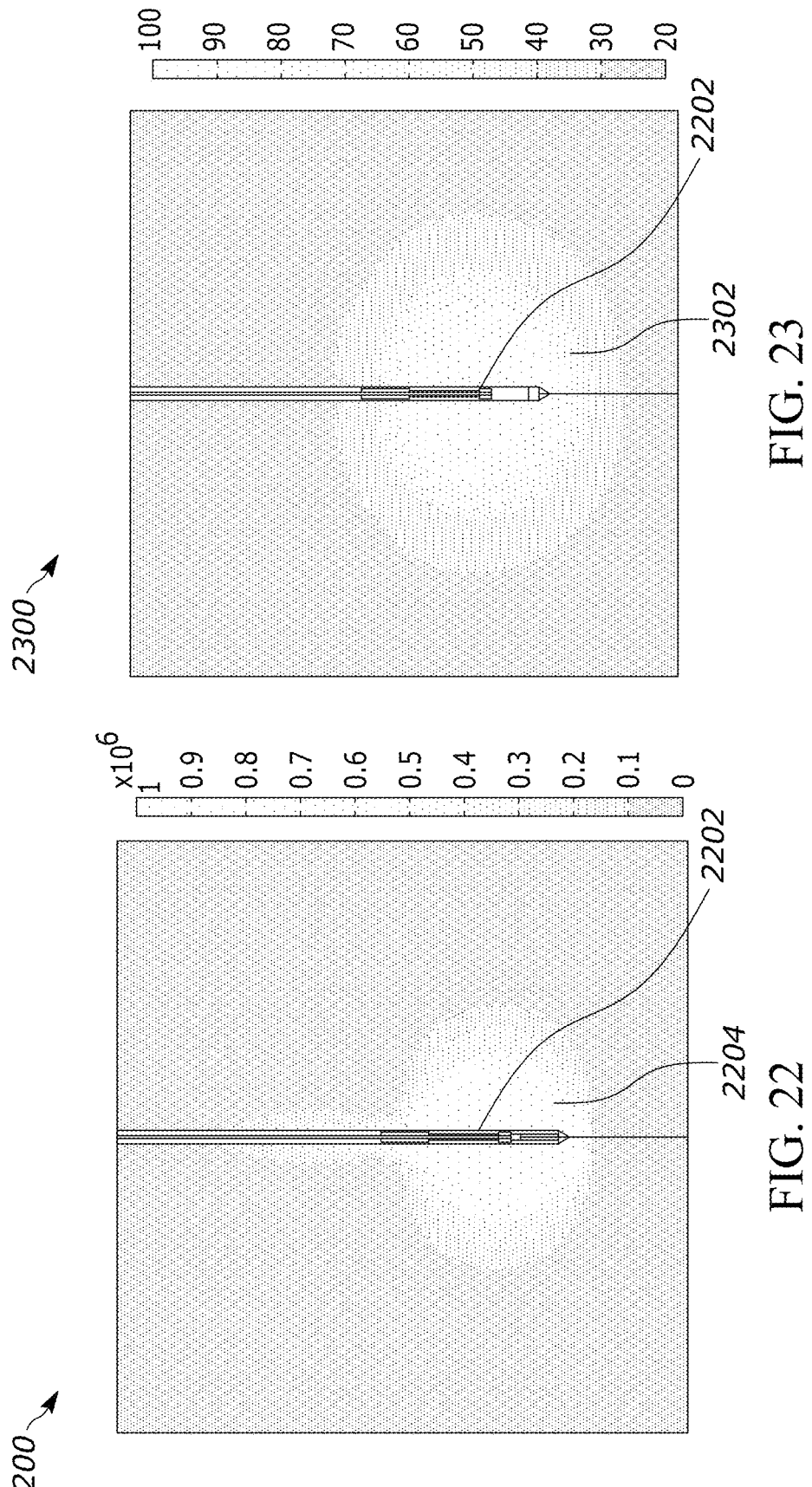
FIG. 22 is an illustration of a simulation map showing a field distribution produced using a probe of the present disclosure.
FIG. 23 is an illustration of another simulation map showing a heating zone produced using a probe of the present disclosure.

In one example, a probe was tested using an ablation simulation. The simulations illustrate heating zones that are produced with a power of 60 Watts for a time period of 10 minutes. A probe was used similar to the probe 1800 (FIG. 18) previously described. As shown in FIGS. 22 and 23, the heating zone exhibits a generally spherical shape. FIG. 22 illustrates an example output of an ablation simulation showing the local specific absorption rate (SAR) of radiofrequency in a simulated tissue. As shown, the heating zone 2204 shows a generally spherical shape around the probe 2202. This operation shows improved performance over other probes.

FIG. 23 is a graphical illustration of the growth of the heating zone 2302 about the probe 2202. FIG. 23 illustrates the temperatures of the heating zone 2302. Similarly to FIG. 22, the heating zone 2302 exhibits a generally spherical shape. Such performance is an improvement over other probes.

The probes of the present disclosure have demonstrated improved performance in laboratory settings in test tissues. In one experiment, a probe was inserted into a test tissue (a bovine liver, in this experiment) and heating using a power level of 80 Watts for 10 minutes while actively cooling the probe with a cooling fluid flowing at a rate of 50 mL/min. A probe was used similar to the probe 1800 (FIG. 18) previously described.

Figures 24, 25, 26:
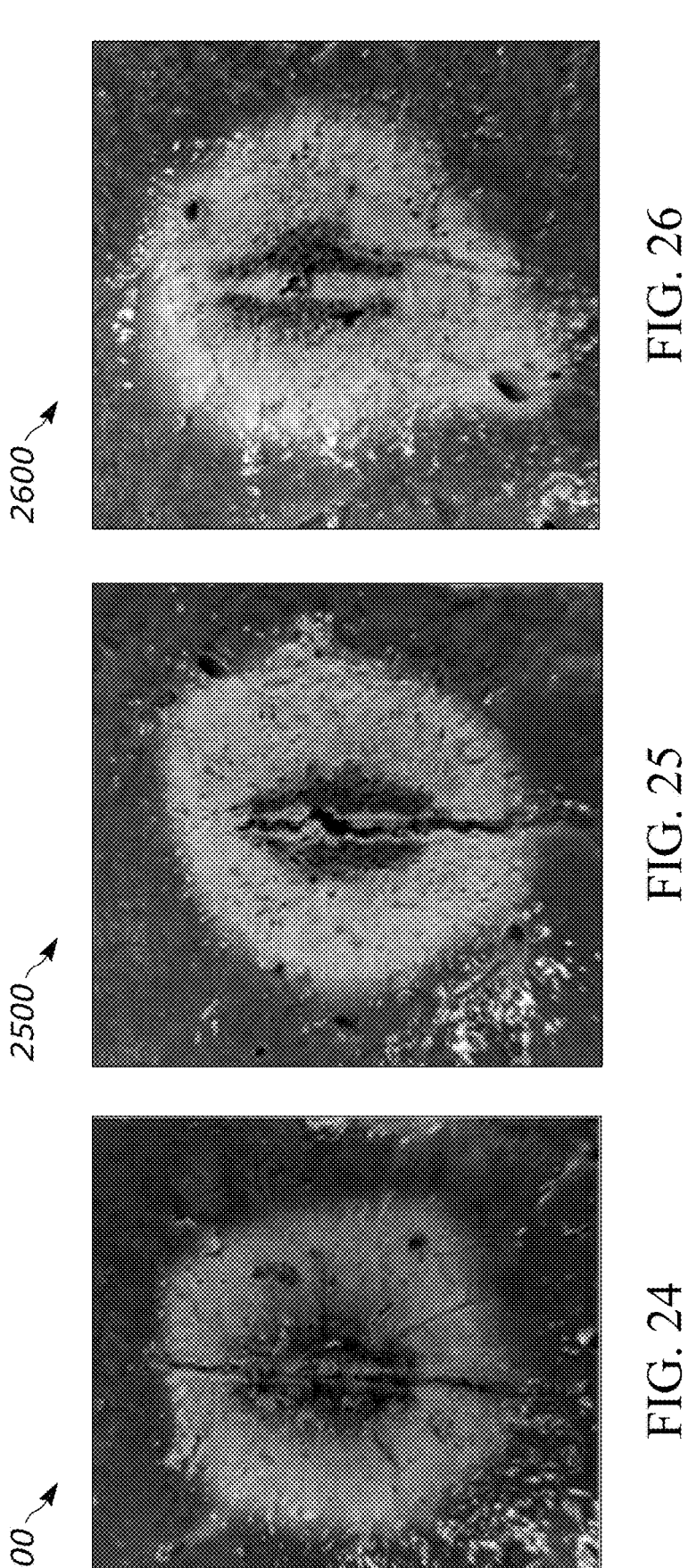
FIG. 24 is an image showing a heating zone in a test tissue created using an example ablation probe of the present disclosure.
FIG. 25 is an image showing another heating zone in another test tissue created using an example ablation probe of the present disclosure.
FIG. 26 is an image showing another heating zone in another test tissue created using an example ablation probe of the present disclosure.

FIGS. 24 to 26 are images of heating zones that were produced in the test tissue after the test was performed as described above. As shown in FIG. 24, the heating zone 2400 produced was generally spherical in shape. The length and width were measured and an axial ratio was determined by dividing the width by the length. In this example, the length of the heating zone was 57.0 mm and the width measured 56.0 mm. This results in an axial ratio of 0.98. FIG. 25 illustrates a heating zone 2500. The heating zone, in this test, measured 60.7 mm in length and 60.0 mm in width. This results in an axial ratio of 0.99. FIG. 26 illustrates another heating zone 2600. The heating zone 2600, in this test measured 63.2 mm in length, 58.8 mm in width. This results in an axial ratio of 0.93. Thus, all test resulted in an axial ratio in excess of 0.90. This performance is improved over other probes.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A microwave ablation probe comprising:
a cable extending in an axial direction;
an antenna coupled to the cable and configured to deliver Radio Frequency (RF) energy;
a shell positioned radially outward of the cable and defining a probe tip;
a choke electrically coupled to an outer conductor of the cable; and
a cooling tube positioned inside the shell and positioned radially outward of the cable, the cooling tube comprising a first portion with a first outer diameter and a second portion with a second outer diameter, the second portion located radially outward of the choke and the second outer diameter being greater than the first outer diameter.

2. The microwave ablation probe of claim 1, wherein the second portion is located closer to the probe tip than the first portion.

3. The microwave ablation probe of claim 1, wherein the first portion of the cooling tube comprises a first length of tubing and the second portion of the cooling tube comprises a second length of tubing, the first length of tubing and the second length of tubing overlapping at a joint.

4. The microwave ablation probe of claim 3, wherein the joint is positioned adjacent the choke on a side away from the probe tip.

5. The microwave ablation probe of claim 1, wherein the first portion of the cooling tube and the second portion of the cooling tube are connected by a transition having a conical shape.

6. The microwave ablation probe of claim 1, wherein the second portion is positioned radially outward of the antenna.

7. The microwave ablation probe of claim 1, wherein the cooling tube comprises a non-metallic material.

8. The microwave ablation probe of claim 1, wherein the cooling tube comprises a polymer material.

9. The microwave ablation probe of claim 1, wherein the cooling tube comprises a rigid support tube, the rigid support tube ending on a side of the choke away from the probe tip.

10. The microwave ablation probe of claim 1, wherein the shell comprises a shell end and a support tube, the shell end comprising a composite material and the support tube comprising a stainless steel tube, the stainless steel tube ending at a side of the choke in a direction away from the probe tip.

11. The microwave ablation probe of claim 1, wherein the choke comprises an outer conductor layer separated from the cable by an insulator layer.

12. The microwave ablation probe of claim 11, wherein the outer conductor layer comprises a metal ink.

13. The microwave ablation probe of claim 11, wherein the outer conductor layer comprises a metallic mesh material.

14. He microwave ablation probe of claim 11, wherein the insulator layer comprises a polyimide ink material.

15. A microwave ablation probe comprising:
a shell comprising a tip for insertion in a target tissue;
a cable positioned inside the shell and configured to deliver RF energy to an antenna;
a choke coupled to the cable; and
a cooling tube positioned between the cable and the shell defining a cooling path for delivery of a cooling fluid, wherein the cooling tube varies in diameter corresponding to a location of the choke.

16. The microwave ablation probe of claim 15, wherein an outer diameter of the shell is less than or equal to 2.1 mm.

17. The microwave ablation probe of claim 15, wherein the cooling tube has a larger diameter at a position at which the cooling tube extends over the choke.

18. The microwave ablation probe of claim 15, wherein an inner surface of the cooling tube defines a supply path for the cooling fluid and an outer surface of the cooling tube defines a return path for the cooling fluid, the choke positioned in the supply path.

19. The microwave ablation probe of claim 15, wherein the cooling tube comprises two lengths of different diameter tubing joined together.

20. The microwave ablation probe of claim 15, wherein the cooling tube comprises a continuous length of tubing with a conical transition between a first diameter portion to a second diameter portion.

* * * * *